(12) United States Patent
Berthon-Jones

(10) Patent No.: US 7,055,522 B2
(45) Date of Patent: *Jun. 6, 2006

(54) PATIENT-VENTILATOR SYNCHRONIZATION USING DUAL PHASE SENSORS

(75) Inventor: Michael Berthon-Jones, Leonay (AU)

(73) Assignee: Resmed Ltd., North Ryde (AU)

( * ) Notice: Subject to any disclaimer, the term of this patent is extended or adjusted under 35 U.S.C. 154(b) by 40 days.

This patent is subject to a terminal disclaimer.

(21) Appl. No.: 10/986,471

(22) Filed: Nov. 11, 2004

(65) Prior Publication Data

US 2005/0081855 A1   Apr. 21, 2005

Related U.S. Application Data

(63) Continuation of application No. 09/661,998, filed on Sep. 14, 2000.

(60) Provisional application No. 60/154,196, filed on Sep. 15, 1999.

(51) Int. Cl.
*F16K 31/02* (2006.01)

(52) U.S. Cl. ............... 128/204.21; 128/204.18; 128/204.23

(58) Field of Classification Search .......... 128/204.18, 128/204.21, 204.22, 204.23, 204.26; 600/529
See application file for complete search history.

(56) References Cited

U.S. PATENT DOCUMENTS

| | | | | |
|---|---|---|---|---|
| 3,807,396 A | * | 4/1974 | Fischel | 128/201.21 |
| 4,520,812 A | * | 6/1985 | Freitag et al. | 128/204.25 |
| 4,596,251 A | * | 6/1986 | Plicchi et al. | 607/20 |
| 4,957,107 A | * | 9/1990 | Sipin | 128/204.21 |
| 5,161,525 A | * | 11/1992 | Kimm et al. | 128/204.26 |
| 5,201,808 A | * | 4/1993 | Steinhaus et al. | 607/20 |
| 5,271,395 A | * | 12/1993 | Wahlstrand et al. | 607/9 |
| 5,307,795 A | * | 5/1994 | Whitwam et al. | 128/204.25 |

(Continued)

FOREIGN PATENT DOCUMENTS

EP   0 452 001 A   10/1991

(Continued)

OTHER PUBLICATIONS

Ward, Eidelamn, Stubbing, Bellemare, & Macklem; "Respiratory sensation and pattern of respiratory muscle activation during diaphragm fatigue"; Journal of Applied Physiology, vol. 65; No. 5; 1988, pp. 2181-2189; XP009038387; United States.

(Continued)

*Primary Examiner*—Henry Bennett
*Assistant Examiner*—Amanda Wieker
(74) *Attorney, Agent, or Firm*—Gottlieb Rackman & Reisman

(57) ABSTRACT

An improved ventilator which delivers ventilatory support that is synchronized with the phase of the patent's respiratory efforts and guarantees a targeted minimum ventilation. Improved synchronization is achieved through an instantaneous respiratory phase determination process based upon measured respiratory airflow as well as measured respiratory effort using an effort sensor accessory, preferably a suprastemal notch sensor. The ventilator processes a respiratory airflow signal, a respiratory effort signal and their respective rates of change to determine a phase using standard fuzzy logic methods. A calculated pressure amplitude is adjusted based upon the calculated phase and a smooth pressure waveform template to deliver synchronized ventilation.

6 Claims, 2 Drawing Sheets

U.S. PATENT DOCUMENTS

| | | | | |
|---|---|---|---|---|
| 5,316,009 | A * | 5/1994 | Yamada | 600/533 |
| 5,316,010 | A * | 5/1994 | Brown | 600/533 |
| 5,390,666 | A * | 2/1995 | Kimm et al. | 128/204.26 |
| 5,540,732 | A * | 7/1996 | Testerman | 607/42 |
| 5,582,163 | A * | 12/1996 | Bonassa | 128/204.26 |
| 5,660,171 | A * | 8/1997 | Kimm et al. | 128/204.23 |
| 5,692,497 | A * | 12/1997 | Schnitzer et al. | 128/204.21 |
| 5,803,065 | A | 9/1998 | Zdrojkowski et al. | |
| 6,152,129 | A * | 11/2000 | Berthon-Jones | 128/200.24 |
| 6,186,142 | B1 * | 2/2001 | Schmidt et al. | 128/204.23 |
| 6,390,091 | B1 * | 5/2002 | Banner et al. | 128/204.21 |
| 6,409,676 | B1 * | 6/2002 | Ruton et al. | 600/532 |
| 6,823,866 | B1 * | 11/2004 | Jafari et al. | 128/204.21 |

FOREIGN PATENT DOCUMENTS

| | | | |
|---|---|---|---|
| WO | WO98/12965 | * | 4/1998 |
| WO | WO 99/61088 | | 12/1999 |

OTHER PUBLICATIONS

EPO Search Report for co-pending application, Mailed Oct. 28, 2004.

Cohen et al, "Breath Detection using Fuzzy Sets and Sensor Fusion", Engineering in Medicine and Biology Society, 1994. Engineering Advances: New Opportunities for Biomedical Engineers. Proceedings of the 16th Annual Conference of the IEEE, vol. 16, pp 1067-1068.

* cited by examiner

PATIENT-VENTILATOR SYNCHRONIZATION USING DUAL PHASE SENSORS

RELATED APPLICATION

This application is a continuation of U.S. application Ser. No. 09/661,998 filed Sep. 14, 2000, now allowed, which claims the priority date of U.S. Provisional Application Ser. No. 60/154,196 filed Sep. 15, 1999.

FIELD OF THE INVENTION

This invention relates to a method and device for providing ventilatory assistance to a patient. More specifically, the invention involves an improved method and device that provides ventilation in phase with a patient's respiratory efforts through the use of a respiratory effort sensor.

BACKGROUND OF THE INVENTION

Devices for providing mechanical ventilation to assist patient respiration are well known. Such ventilator devices have been used to help patients with such ailments as severe lung disease, chest wall disease, neuromuscular disease and other diseases of respiratory control. Generally, a ventilator provides air or oxygen-enriched air to a patient at pressures that are higher during inspiration and lower during expiration.

Several types of ventilator devices exist. These types include bi-level ventilators, proportional assist ventilators and servo-controlled ventilators. Each type of ventilator utilizes different methods for assisting with patient respiration and achieves different goals.

Bi-level ventilators provide the simplest level of support. These ventilators supply a mask pressure $P(t)$ which is higher by an amplitude $A$ from an initial pressure $P_0$ when respiratory airflow $f(t)$ is inspiratory, $f(t)>0$, than when respiratory airflow is expiratory, $f(t) \leq 0$.

| | | |
|---|---|---|
| $P(t) = P_0 + A$ | $f(t) > 0$ | (inspiration) |
| $P(t) = P_0$ | otherwise | (expiration) |

Thus, these devices supply a fixed degree of support $A$. However, they do not guarantee any particular ventilation when, for example, the patient's efforts are inadequate.

Proportional assist ventilators represent an attempt to provide support more closely in phase with the patient's respiratory efforts. Proportional assist ventilators provide mask pressure as follows:

| | | |
|---|---|---|
| $P(t) = P_0 + R\,f(t) + E_{LC} \int f(t)dt$ | $f(t) > 0$ | (inspiration) |
| $P(t) = P_0 + R\,f(t)$ | otherwise | (expiration) | where R is a substantial fraction of the patient's airway resistance, and $E_{LC}$ is a substantial fraction of the patient's lung plus chest wall elastance. So long as there is no leak, this provides support much more closely in phase with a patient's respiratory efforts. However, again, in the case of a patients efforts being inadequate, for example, due to reduced chemoreflex control of breathing during sleep, there is no guaranteed minimum ventilation.

One method of ensuring an adequate degree of ventilatory support is to use a servo ventilator, which adjusts the degree of support $A$ to servo-control instantaneous ventilation $V(t)$ to equal a target ventilation $V_{TGT}$:

| | |
|---|---|
| $P(t) = P_0 + A$ | $f(t) > 0$, or time since the start of the last inhalation $> T_{MAX}$ |
| $P(t) = 0$ | otherwise | where:

$A = G \int (V(t) - V_{TGT}) dt$ $V(t) = 0.5\,\text{abs}(f(t))$ $A_{MIN} < A < A_{MAX}$.

In this ventilator, $V(t)$ is one half the absolute value of the respiratory airflow, G is the gain of the integral servo-controller, a value of 0.3 cmH$_2$O per L/min error in ventilation per second being suitable, and $A_{MIN}$ and $A_{MAX}$ are limits set on the degree of support $A$ for comfort and safety, 0.0 and 20.0 cmH$_2$O being generally suitable. Unfortunately, while this method achieves a guaranteed minimum ventilation, there is little attempt to keep the support precisely in phase with the patient's own respiratory efforts. Rather, the system merely makes a step change in pressure at the start and end of inspiration.

In a more advanced servo-controlled ventilator, both guaranteed ventilation and phase synchronization is achieved. This apparatus is the subject of the commonly owned International Patent Application entitled "Assisted Ventilation to Match Patient Respiratory Need," International Publication Number WO98/12965 (hereinafter referred to as "AutoVPAP"). The AutoVPAP apparatus provides an instantaneous mask pressure $P(t)$ based upon a substantial fraction of the patient's airway resistance R, respiratory airflow $f(t)$, an amplitude A, and an estimation of the patient's instantaneous respiratory phase $\Phi$ as applied to a smooth pressure waveform template $\Pi(\Phi)$ as follows:

| | |
|---|---|
| $P(t) = P_0 + R\,f(t) + A\,\Pi(\Phi)$ for all $f(t)$ | (inspiration and expiration) | where:

$A = G \int (V(t) - V_{TGT}) dt$ $V(t) = 0.5\,\text{abs}(f(t))$ $A_{MIN} < A < A_{MAX}$.

In estimating the respiratory phase, the AutoVPAP apparatus uses a respiratory airflow signal and its derivative as input data for a set of fuzzy logic rules that are associated with particular phases of respiration. Using the results of the evaluations of the rules, a single phase value is derived and used as the instantaneous respiratory phase. Thus, the degree of ventilatory support is varied in phase with the patient's respiration. Moreover, as the calculation of A is based upon a target ventilation $V_{TGT}$, a guaranteed level of ventilation is provided.

However, in this AutoVPAP system, room for improvement exists in the phase determination due to the problem of leak. Mask and/or mouth leak is ubiquitous during noninvasive ventilatory support using a mask, and is particularly problematical during sleep. Leak causes mis-measurement of the respiratory airflow, and therefore can severely interfere with patient-machine synchronization.

BRIEF DESCRIPTION OF THE INVENTION

An objective of the present invention is to provide a method and apparatus to supply ventilatory assistance precisely in phase with a patient's spontaneous ventilatory efforts provided these efforts are adequate to maintain a specified target ventilation.

A further objective of the present invention is to provide a method and apparatus to guarantee at least a specified target ventilation, even in the event that the patient's efforts become irregular or cease.

Additional objectives will be apparent from the description of the invention as contained herein.

In its broadest aspects, the present invention involves an improved ventilator which delivers ventilatory support that is synchronized with the phase of a patient's respiratory efforts and guarantees a targeted minimum ventilation. The device provides ventilatory support to a patient based in part upon a calculated instantaneous mask pressure using a general method similar to that of the previously described AutoVPAP system. However, the respiratory phase determination is improved by using data representing both respiratory airflow and respiratory effort.

More specifically, in estimating the respiratory phase, the device utilizes a respiratory airflow signal and preferably its rate of change. The degree of membership of the respiratory airflow signal in each of the fuzzy sets zero, positive, large positive, negative, and large negative is calculated using suitable membership functions. Similarly, the degree of membership of the derivative of the respiratory airflow signal in each of the fuzzy sets steady, increasing, increasing fast, decreasing and decreasing fast is calculated using suitable membership functions. The degrees of membership in these classes are used in a set of fuzzy logic inference rules. Each fuzzy inference rule is associated with a particular phase of respiration.

Although many variations are possible, in the preferred embodiment, the inference rules relating to respiratory airflow are as follows:

1. If the airflow is zero and increasing fast, then the phase is 0 revolutions.
2. If the airflow is large positive and steady, then the phase is 0.25 revolutions.
3. If the airflow is zero and falling fast, then the phase is 0.5 revolutions.
4. If the airflow is large negative and steady, then the phase is 0.75 revolutions.
5. If the airflow is zero and steady and the 5-second low-pass filtered absolute value of the respiratory airflow is large, then the phase is 0.9 revolutions.
6. If the airflow is positive and the phase is expiratory, then the phase is 0.1 revolutions.
7. If the airflow is negative and the phase is inspiratory, then the phase is 0.6 revolutions.
8. If the 5-second low-pass filtered absolute value of the respiratory airflow is small, then the phase in the respiratory cycle is increasing at a fixed rate equal to the patient's expected respiratory rate.
9. If the 5-second low-pass filtered absolute value of the respiratory airflow is large, then the phase in the respiratory cycle is increasing at a steady rate equal to the existing rate of change of phase, low-pass filtered with a time constant of 20 seconds.

In the invention, the device combines additional fuzzy inference rules based upon an effort signal from an effort sensor. The effort sensor is not dependent on measured airflow and as such is immune to errors associated with leak. The effort signal and preferably its rate of change are used as input values for membership functions for the additional fuzzy inference rules that are also associated with particular phases. The membership functions are used to calculate the degree of membership of the effort signal in each of the fuzzy sets zero, medium and large, and the degree of membership of its derivative in each of the fuzzy sets increasing moderately, increasing fast, decreasing moderately and decreasing fast.

In the preferred embodiment, the inference rules relating to respiratory effort are as follows:

10. If the effort signal is zero and increasing fast, then the phase is 0 revolutions.
11. If the effort signal is medium and increasing moderately, then the phase is 0.2 revolutions.
12. If the effort signal is large and decreasing fast, then the phase is 0.5 revolutions.
13. If the effort signal is medium and decreasing moderately, then the phase is 0.7 revolutions.

In general, the phase values need not be these exact values, but can approximate them.

In a process similar to that of the AutoVPAP system, all of the fuzzy inference rules are evaluated and a single phase value is derived and taken as the instantaneous respiratory phase of the patient. This allows the degree of support provided by the device to remain in phase with the patient's respiration.

In the preferred embodiment, the effort sensor is a suprastemal notch sensor. However, alternative embodiments of the invention may utilize other effort sensors including, for example, an esophageal pressure sensor or an electromyograph.

DETAILED DESCRIPTION OF THE INVENTION

Figure 1:
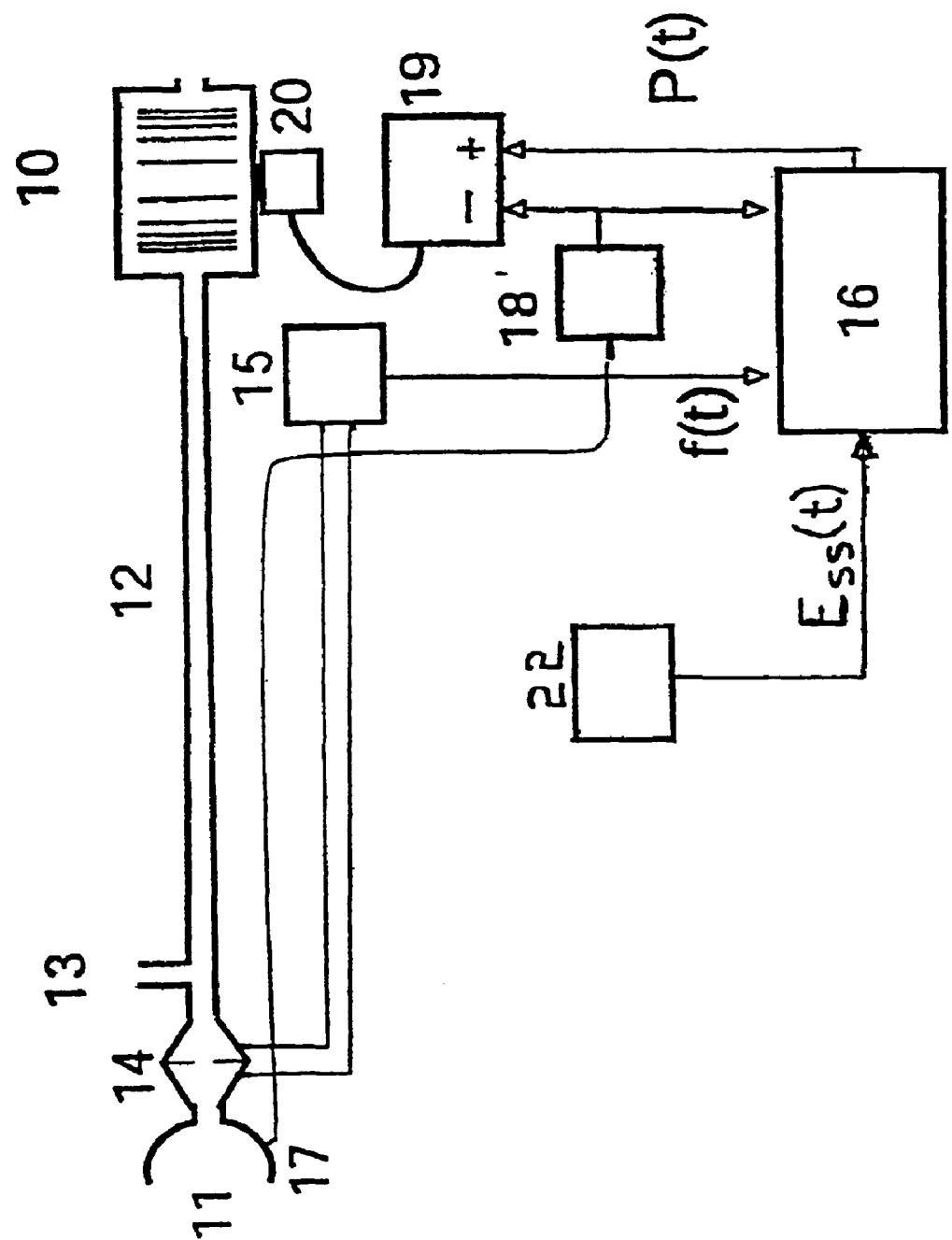
FIG. 1 depicts the components of a servo-controlled ventilator with an effort sensor.

A servo-controlled ventilator useful for accomplishing the present invention is shown in FIG. 1. A blower 10 supplies air under pressure via delivery tube 12 to a mask 11. Exhaust gas is vented via exhaust 13. Mask flow is measured using pneumotachograph 14 and differential pressure transducer 15 to derive flow signal f(t). Mask pressure is measured at pressure tap 17 using pressure transducer 18. Respiratory effort is measured by an effort sensor 22 to yield an effort signal $E_{ss}(t)$. Flow, effort and pressure signals are sent to microcontroller 16 which implements the processing shown in FIG. 2 to derive a pressure request signal P(t). The actual measured pressure and pressure request signal P(t) are fed to motor servo 19 which controls blower motor 20 to produce the desired instantaneous mask pressure. An example of this type of ventilator, without an effort sensor 22, is the subject of International Publication No. WO 98/12965, which is also disclosed in related U.S. application Ser. No. 08/935,785. An additional example is disclosed in International Publication No. WO 99/61088, which is also contained in related U.S. application Ser. No. 09/316,432. The foregoing U.S. applications are hereby incorporated by reference.

In the preferred embodiment of the present invention, a suprastemal notch sensor is used as the effort sensor 22 to generate the effort signal. The sensor is more fully described in a commonly owned patent application entitled "Measurement of Respiratory Effort Using a Suprasternal Sensor," application Ser. No. 09/396,031 filed on Sep. 15, 1999. The suprasternal notch sensor measures changes in the suprasternal notch. Increasing inspiratory efforts cause the skin of the suprasternal notch to retract. An optical sensor generates an electrical signal that is an increasing function of inspiratory effort derived by measuring changes in the depth of the skin of the suprasternal notch. In a further commonly owned patent application filed on Sep. 15, 1999, entitled "Ventilatory Assistance Using an External Effort Sensor," application Ser. No. 09/396,032, the effort signal is used to trigger a bilevel ventilator. Both applications are hereby incorporated by reference.

Figure 2:
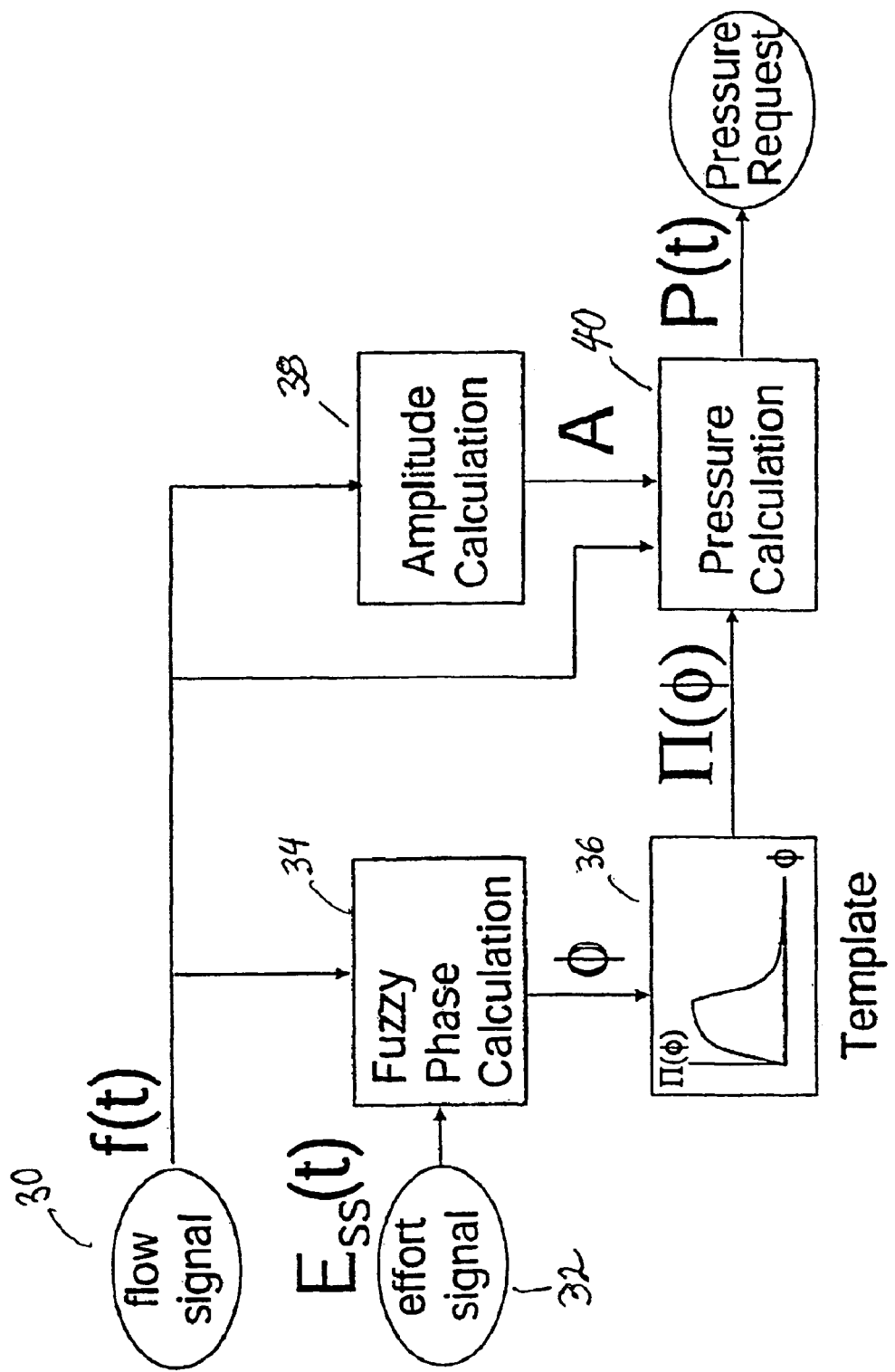
FIG. 2 depicts the steps involved in determining the delivered pressure level, including use of the effort signal.

With reference to FIG. 2, using the aforementioned system of FIG. 1, several steps are used to derive the pressure request signal P(t). In steps 30 and 32, an instantaneous airflow signal f(t) and an effort signal $E_{ss}(t)$ are generated. In step 34, labeled Fuzzy Phase Calculation, the system calculates the phase Φ in the respiratory cycle as a continuous variable using a set of fuzzy inference rules. The fuzzy inference rules are based upon both respiratory airflow and respiratory effort.

The preferred rules with respect to respiratory airflow are those described above, rules 1–9, although many other inference rules can be developed based upon respiratory airflow. The fuzzy extents, or the degrees of truth, to which the airflow is in fuzzy sets zero, positive, large positive, negative, and large negative, and the 5-second low-pass filtered absolute value is small and large, are determined with suitable membership functions using the measured respiratory airflow f(t). Similarly, the fuzzy extents to which the airflow is in fuzzy sets steady, increasing fast and decreasing fast are determined with suitable membership functions using the change in respiratory airflow df(t)/dt. The fuzzy extents to which the phase is a member of the fuzzy sets expiratory and inspiratory is determined by membership functions using a previously calculated instantaneous phase. This approach using respiratory airflow to determine phase is that disclosed in International Publication Nos. WO 98/12965 and WO 99/61088.

Rules 1–4 estimate the phase directly from the instantaneous respiratory airflow. Rule 5 permits an expiratory pause, whose length may be long if the patient has recently been breathing adequately, and short or zero if the patient is not breathing. Rules 6–7 provide for quick resynchronization in the event that the patient breathes irregularly. Rule 8 provides the equivalent of a timed backup, in which, to the extent that the patient has stopped breathing or is not adequately breathing, the ventilator will cycle at a suitable fixed rate. Rule 9 provides that to the extent that the patient is breathing adequately, the ventilator will tend to track the patient's recent average respiratory rate. This is particularly appropriate for patients with cardiac failure and Cheyne-Stokes breathing, whose respiratory rates tend to be extremely steady despite rhythmic changes in amplitude.

An effect of the changing degree of activation of rules 8 and 9 is that, to the fuzzy extent that the instantaneous ventilation equals or exceeds the target ventilation, ventilatory support will be provided in phase with the patient's own respiratory efforts, and to the extent that the instantaneous ventilation is less than the target ventilation, ventilatory support will be provided at a pre-set rate.

In an elaboration of this embodiment, the weighting of rules 1–6 can be made proportional to the fuzzy extent that the instantaneous ventilation is large compared with the target ventilation, thereby reinforcing the behavior described in the previous paragraph.

In a further elaboration, the weighting of rules 1–6 and also of rule 9 can be made smaller and the weighting of rule 8 can be made larger, if the leak is large or if there is a sudden change in the leak. In this way, to the extent that the respiratory airflow signal is of high quality, ventilatory support will be provided as described in the preceding paragraphs, but to the extent that the respiratory airflow signal is of poor quality and it is difficult to synchronize reliably with the patient's efforts, or to know if the patient's efforts are adequate, ventilatory support will be provided in an orderly manner at a predetermined fixed rate.

As previously mentioned, the Fuzzy Phase Calculation of step 34 also involves fuzzy inference rules relating to respiratory effort. To this end, the invention takes the effort signal $E_{ss}(t)$ from the effort sensor 22 and processes additional fuzzy inference rules.

The general method for developing and using these additional fuzzy inference rules for the effort signal is the same as the method described in International Publication Nos. WO 98/12965 and WO 99/61088. Generally, various features, such as the point of start of inspiration, are identified on a graph of effort versus phase, and for each phase, corresponding fuzzy rules are developed. For example, a suitable rule for the point "start of inspiration" could be "effort signal is small and the second derivative of the effort signal with respect to time is large positive." Membership functions, would cause that rule to be maximally activated at or near the start of inspiration. Preferably, the exact phase at the moment of maximal activation should be determined empirically. In the current example, the maximum activation will be at a phase shortly after the actual moment of start of inspiration, say 0.05 revolutions, and this is the best phase to associate with the rule. The more features that are identified and assigned a rule and a phase, the smoother will be the resultant determination of phase.

The illustrative additional fuzzy inference rules relating to the effort signal $E_{ss}(t)$ from the suprasternal effort sensor and the rate of change in the signal, $dE_{ss}(t)/dt$, are rules 10–13 provided above.

The fuzzy extents to which the effort signal is in fuzzy sets zero, medium and large are calculated with appropriate membership functions using $E_{ss}(t)$. Similarly, the fuzzy extents to which the effort signal is in fuzzy sets increasing moderately, increasing fast, decreasing moderately or decreasing fast are determined with appropriate membership functions using the rate of change of the effort signal, $dE_{ss}(t)/dt$. Preferably, the effort signal is normalized for amplitude prior to calculation of degrees of membership, for example, by dividing by the amplitude of the effort signal calculated over a long period compared with a breath, for example, 10–30 seconds.

Continuing with FIG. 2 and the Fuzzy Phase Calculation of step 34, each of the rules in the combined set of fuzzy inference rules is evaluated to determine a degree of activation G(n) by using a standard fuzzy inference method. For example, with respect to rule 12, using one such method assuming a unit weighting of rules, if (a) the degree of truth for the membership function "the effort signal is large" evaluates to 0.6 and (b) the degree of truth for the membership function "the effort signal is decreasing fast" evaluates to 0.4, and a fuzzy logic "AND" operator is applied, then the degree of activation for G(12) would be 0.4.

Additionally, each of the 13 fuzzy inference rules associates a particular rule with a particular phase Φ(n). For example, as shown above, rule 12 is associated with Φ(12) =0.5 revolutions. Then, using the degree of activation G(n) for each Φ(n), a single value representing the instantaneous respiratory phase Φ is calculated in a defuzzification step using the formula:

Φ=arctan {Σ[G(n)sin Φ(n)]/Σ[G(n)cos Φ(n)]}.

The phase Φ is then used in step 36 of FIG. 2 to derive a value from the smooth pressure waveform template Π(Φ).

Step 38, labeled "Amplitude Calculation," involves a calculation of an instantaneous amplitude of pressure support A, chosen to servo-control instantaneous ventilation to, on average, equal a target $V_{TGT}$, by the following formula:

A=G ∫(V(t)-$V_{TGT}$)dt

V(t)=0.5 abs (f(t))

$A_{MIN}$<A<$A_{MAX}$

Finally, in the "Pressure Calculation" step 40, the system calculates the desired degree of ventilatory support P(t) from the calculated amplitude A, a substantial fraction of the patient's airway resistance R, respiratory airflow f(t), and the smooth pressure waveform template Π(φ):

P(t)=$P_0$+R f(t)+AΠ(Φ)

The Amplitude Calculation and Pressure Calculation steps as just described are comparable to the steps in International Publication Nos. WO 98/12965 and WO 99/61088.

In the preferred embodiment of the invention, the effort sensor is an accessory that can be added or removed at will from a ventilator such as an AutoVPAP system in order to achieve improved synchronization with the patient. If the effort sensor falls off the patient, fails, is electrically unplugged or is otherwise removed, then rules (10) to (13) will have no effect on the phase determination or, in other words, the rules will have no degree of activation. In this event, the device will behave as a simple servo-controlled ventilator such as the AutoVPAP device. The patient will continue to be ventilated, with ventilatory support provided approximately in phase with respiratory airflow and therefore approximately in phase with respiratory effort. Thus, the degree of support will be sufficient to guarantee that instantaneous ventilation on average equals or exceeds the target ventilation, but the precise timing information and improved immunity to the effects of leaks will be lost.

While the described embodiment of the present invention makes use of a suprasternal effort sensor, effort signals from other sensors may also be utilized. Other forms of effort signal include, for example, an effort signal derived from esophageal pressure generated by a pressure transducer implanted in the chest that sends a signal via telemetry. Alternatively, an electromyogram signal from an electromyograph could be used without requiring any modification to the invention. Moreover, multiple effort sensors can be utilized simply with the addition of extra fuzzy inference rules relating to the additional effort sensors.

Although the invention has been described with reference to particular embodiments, it is to be understood that these embodiments are merely illustrative of an application of the principles of the invention. For example, one embodiment of the invention might utilize a set of rules to determine phase in which some of the rules determine phase based solely upon the magnitude of the respiratory airflow and the rate of change of an effort signal. Alternatively, some rules may determine phase based upon the magnitude of the effort signal and the rate of change of respiratory airflow. Numerous modifications, in addition to the illustrative embodiments of the invention discussed herein may be made and other arrangements may be devised without departing from the spirit and scope of the invention.

The invention claimed is:

1. A method of providing synchronized ventilatory support to a patient comprising the steps of:
   providing apparatus to deliver ventilatory support to a patient, the apparatus also measuring both respiratory airflow and respiratory effort;
   determining at least one instantaneous phase of respiration of the patient at least in part from both measured respiratory airflow and respiratory effort,
   calculating a desired pressure value using the determined phase and a desired ventilation pressure amplitude; and
   delivering ventilation to said patient in accordance with said desired pressure value.

2. The method of claim 1 wherein said respiratory effort is sensed by a sensor selected from a group of effort sensors that are independent of a leak in airflow that may affect respiratory airflow measurement including:
   (a) a suprasternal notch sensor;
   (b) an esophageal pressure effort sensor; and
   (c) an electromyograph.

3. The method of claim 2 wherein the phase determining step comprises evaluating fuzzy inference rules relating to a signal from said respiratory effort sensor.

4. The method of claim 3 wherein said phase determining step further comprises evaluating fuzzy inference rules relating to the rate of change of said signal from said respiratory effort sensor.

5. The method of claim 4 wherein said phase determining step further includes the sub-step of evaluating fuzzy logic inference rules relating to the measured respiratory airflow.

6. The method of claim 5 wherein said phase determining step further includes the sub-step of evaluating fuzzy logic inference rules relating to the rate of change of the measured respiratory airflow.

* * * * *